(12) United States Patent
Da Silva et al.

(10) Patent No.: US 6,647,285 B2
(45) Date of Patent: Nov. 11, 2003

(54) OPTICAL PROBE WITH LIGHT FLUCTUATION PROTECTION

(75) Inventors: Luiz B. Da Silva, Danville, CA (US); Charles L. Chase, Dublin, CA (US)

(73) Assignee: The Regents of the University of California, Oakland, CA (US)

( * ) Notice: Subject to any disclaimer, the term of this patent is extended or adjusted under 35 U.S.C. 154(b) by 58 days.

(21) Appl. No.: 09/997,470

(22) Filed: Nov. 29, 2001

(65) Prior Publication Data

US 2003/0100835 A1 May 29, 2003

(51) Int. Cl.[7] .................................................. A61B 6/00
(52) U.S. Cl. ...................... 600/478; 600/473; 600/476; 600/425; 388/54; 388/115
(58) Field of Search ................................ 600/473, 476, 600/425, 478; 385/54, 115

(56) References Cited

U.S. PATENT DOCUMENTS

| | | | |
|---|---|---|---|
| 5,303,026 A | 4/1994 | Strobl et al. | 356/318 |
| 5,349,954 A | 9/1994 | Tiemann et al. | 128/634 |
| 5,792,053 A | 8/1998 | Skladnev et al. | 600/407 |
| 5,800,350 A | 9/1998 | Coppleson et al. | 600/372 |
| 5,941,834 A | 8/1999 | Skladnev et al. | 600/587 |
| 6,026,323 A | 2/2000 | Skladnev et al. | 600/547 |
| 6,109,270 A | 8/2000 | Mah et al. | 128/920 |
| 6,366,726 B1 * | 4/2002 | Wach et al. | 385/115 |
| 6,487,349 B2 * | 11/2002 | Wach et al. | 385/115 |

FOREIGN PATENT DOCUMENTS

| | | | |
|---|---|---|---|
| EP | 0 582 686 B1 | 8/1998 | A61N/5/06 |
| EP | 0 872 211 B1 | 7/2000 | A61B/5/00 |
| EP | 1 092 385 A2 | 4/2001 | A61B/5/00 |

\* cited by examiner

*Primary Examiner*—Marvin M. Lateef
*Assistant Examiner*—Jeoyuh Lin
(74) *Attorney, Agent, or Firm*—Eddie E. Scott; Alan H. Thompson

(57) ABSTRACT

An optical probe for tissue identification includes an elongated body. Optical fibers are located within the elongated body for transmitting light to and from the tissue. Light fluctuation protection is associated with the optical fibers. In one embodiment the light fluctuation protection includes a reflective coating on the optical fibers to reduce stray light. In another embodiment the light fluctuation protection includes a filler with very high absorption located within the elongated body between the optical fibers.

9 Claims, 4 Drawing Sheets

OPTICAL PROBE WITH LIGHT FLUCTUATION PROTECTION

The United States Government has rights in this invention pursuant to Contract No. W-7405-ENG-48 between the United States Department of Energy and the University of California for the operation of Lawrence Livermore National Laboratory.

BACKGROUND OF THE INVENTION

1. Field of Endeavor

The present invention relates to tissue recognition and more particularly to a probe system for tissue recognition.

2. State of Technology

A New Release dated Jan. 10, 2001 by the Lawrence Livermore National Laboratory operated by the University of California provides the following information, "The pain and anxiety women experience undergoing breast cancer tests and awaiting the results may soon be lessened thanks to a new, minimally invasive diagnostic tool that can instantly detect cancerous tissue. Lawrence Livermore National Laboratory has partnered with San Jose-based BioLuminate, Inc. to develop "Smart Probe," a tool for earlier, more accurate breast cancer detection that removes no tissue and is expected to achieve accuracy levels comparable to surgical biopsies in detecting cancerous cells.

The BioLuminate "Smart Probe," smaller than the needle used in routine blood tests, is inserted into breast tissue after an initial screening indicates an area of concern. The probe looks for multiple known indicators of breast cancer, instantaneously providing physicians with information they can use to determine whether more invasive and costly tests are necessary. The results of the "Smart Probe" procedure are immediately available to patients, helping relieve anxiety. First human studies using the device are expected to begin this spring at sites to be selected in Northern California. "Physicians have been seeking a way to acquire more specific information about a suspected cancer site before performing a biopsy or surgery," said Neil Gorrin, MD, Assistant Chief of Surgery at Kaiser Permanente Medical Center in South San Francisco. "The "Smart Probe" not only is less invasive, but it provides several specific measurements of known cancer indicators in real time, which will improve our chances of making the right diagnosis and treatment plan for the patient."

Fewer Unnecessary Biopsies—Breast cancer is the second leading cause of death among women in the United States. Last year in the U.S., 182,800 women were diagnosed with breast cancer and more than 40,800 died of the disease. In the U.S. each week, approximately 16,000 women undergo unnecessary, surgical breast biopsies on suspicious tissue that turns out benign. In addition, physicians miss about 4,600 cases of breast cancer each week during physical examinations and mammogram reviews. "By using the BioLuminate 'Smart Probe' before biopsies are performed on suspicious lesions, many unnecessary surgeries can be eliminated," said Richard Hular, President and CEO of BioLuminate. "Not only is this a great benefit for the patient, it also has the potential to save the U.S. healthcare system over \$2 billion annually."

Cancer Indicators Measured in Real Time—Once a mammogram or physical exam has detected a possible malignant lump, "Smart Probe" is inserted into the tissue and guided to the suspicious region. Sensors on the tip of the probe measure optical, electrical and chemical properties that are known to differ between healthy and cancerous tissues. The "Smart Probe" can detect multiple (5 to 7) known indicators of breast cancer. Tissue measurements are made in real time in both normal and suspect tissue. "Smart Probe's" sensors begin gathering information the moment the probe is inserted into tissue. Computer software compares the real-time measurements to a set of known, archived parameters that indicate the presence or absence of cancer. The results are displayed instantly on a computer screen. "The key technology and experience that Lawrence Livermore Lab has to offer will allow the 'Smart Probe' to be much smaller than first conceived, and acquire data more accurately," said Luiz Da Silva, Ph.D, Livermore's Associate Medical Technology Program Leader and primary investigator for the "Smart Probe." "In addition, we will have the capacity to add additional measurements if necessary."

U.S. Pat. No. 5,303,026 for apparatus and method for spectroscopic analysis of scattering media by Karlheinz Strobl, Irving J. Bigio, and Thomas R. Loree, patented Apr. 12, 1994 provides the following background information, "Attempts at in situ real-time diagnostics for complex biological media, have been only marginally successful because of limitations in the spectroscopic techniques that are applicable. Conventional fluorescence spectroscopy is generally unable to resolve differences among similar biological tissue samples (or subtle differences in a given tissue sample) and has generally not proven reliable in detecting malignancy except with the aid of drugs such as hematoporphyrin derivatives which are used as targeting fluorescers."

U.S. Pat. No. 5,349,954 for a tumor tissue characterization apparatus and method by Jerome J. Tiemann and Fay A. Marks, patented Sep. 27, 1994 provides the following background information, "In a conventional procedure, a radiologist performs x-ray mammography. If an abnormal breast process recorded on the resulting mammograms is considered suspicious, a surgical biopsy can be ordered. Immediately prior to the biopsy, the radiologist takes several more views or projections of the breast during preoperative localization of the abnormality and marks the location of the suspicious abnormality by impaling the region with a thin, hooked guide wire. The patient is then taken to an operating room and a surgeon performing the biopsy follows the hooked wire guide to the precise location of the suspected abnormality. The most common form of biopsy involves surgically removing the suspected region. One of the less invasive forms of biopsy, stereotactic fine needle aspiration biopsy, aspirates a small amount of cells for cytologic analysis. The advantages of this technique are that it is minimally invasive, is accurate to less than 2 mm in lesion localization, has sensitivity greater than 90%, and is less expensive than surgical biopsies. But since small (22 gauge) needles are used, cytology on the small amount of material removed is not easy. Far more accurate is large-core needle biopsy (using stereotactic positioning or ultrasound guidance), another alternative to surgical biopsy. Core biopsies remove a 1 mm.times.17 mm core of tissue (if a 14 gauge needle is used) for standard histological examination. However, benign histological diagnoses are difficult to make. In fact, for both fine needle aspiration biopsy and core biopsy, the techniques are only useful when they return a positive result for malignancy. In all other cases, the suspicious lesion must undergo incisional or excisional surgical biopsy. False negatives in analyzing an x-ray mammogram occur when benign tumors or "normal" breast tissue with radiological densities similar to cancer completely or partially mask a malignant tumor which does not exhibit primary or secondary mammographic signs of carcinema. False positives are also problematic because they reduce the acceptability of mammography by the general public and lead to unnecessary biopsies."

U.S. Pat. No. 5,800,350 for an apparatus for tissue type recognition by Coppleson et al, patented Sep. 1, 1998, provides the following background information, "The early detection of tissues displaying pre-cancer or cancer modifications is important for successful medical treatment. Presently-used detection techniques suffer from inaccuracy and are subject to operator error as well as being time-consuming. A good example of this is the Pap smear for cervical cancer. X-ray diagnosis, which can also be used for detecting advanced cancer modifications, can lead to detrimental exposure to radiation. A positive result produced by a Pap smear test is generally followed by a visual examination using a colposcope which provides a magnified view of the cervix. Suspect regions of the cervix are evaluated by a skilled practitioner who then makes a subjective judgement of the tissue observed. There are many tissue types in the cervix, some of which display analogous appearances, including visual and textural characteristics, that make clinical diagnosis very difficult and subject to error. Similar subjective assessments play a major role in the detection and treatment of other locations of neoplastic pre-activity and activity, for example skin melanoma. Methods and devices have been developed in an attempt to use measurements of physical characteristics of the tissue for distinguishing cancerous tissue from non-cancerous tissue. Electrical measurements of the skin or tissue have been used. Such electrical measurements on their own do not provide the information needed for an effective diagnosis."

U.S. Pat. No. 6,026,323 for a tissue diagnostic system by Skladnev et al, patented Feb. 15, 2000, provides the following background information, "The identification of tissue type based upon responses to incident light and/or electrical stimulation is well known. This has led to diagnostic techniques and apparatus for identifying tissue types such as cancerous or pre-cancerous. Existing techniques for identifying cancers run the gamut from microscopic examination of tissue smears by trained cell pathologists, to the study of the fluorescence, electrical and other physical properties of tissues. Much research has been devoted to the identification and comparison of optical and electrical characteristics of healthy and damaged tissue in the hope that it could lead to new diagnostic techniques."

U.S. Pat. No. 6,109,270 for a multimodality instrument for tissue characterization by Robert W. Mah and Russell J. Andrews, patented Aug. 29, 2000 provides the following background information, "Existing medical instruments provide general diagnoses for the detection of tissue interface such as normal tissue, cancer tumor, etc. However, such detection has been limited clinically to tactile feedback, temperature monitoring, and the use of a miniature ultrasound probe for tissue differentiation during surgical operations. Stereotactic computed tomography (CT) scanners, magnetic resonance imaging (MRI) devices, and similar other instruments provide guided brain biopsy and preoperative scans for use in neurosurgical surgeries. These scans allow samples of brain tissue to be obtained with some degree of accuracy. However, existing devices provide diagnostic data of limited use, particularly in neurosurgery, where the needle used in the standard stereotactic CT or MRI guided brain biopsy provides no information about the tissue being sampled. The tissue sampled depends entirely upon the accuracy with which the localization provided by the preoperative CT or MRI scan is translated to the intracranial biopsy site. Any movement of the brain or the localization device (e.g., either a frame placed on the patient's head, or fiducials/anatomical landmarks which are in turn related to the preoperative scan) results in an error in biopsy localization. Also, no information about the tissue being traversed by the needle (e.g., a blood vessel) is provided. Hemorrhage due to the biopsy needle severing a blood vessel within the brain is the most devastating complication of stereotactic CT or MRI guided brain biopsy."

SUMMARY OF THE INVENTION

Features and advantages of the present invention will become apparent from the following description. Applicants are providing this description, which includes drawings and examples of specific embodiments, to give a broad representation of the invention. Various changes and modifications within the spirit and scope of the invention will become apparent to those skilled in the art from this description and by practice of the invention. The scope of the invention is not intended to be limited to the particular forms disclosed and the invention covers all modifications, equivalents, and alternatives falling within the spirit and scope of the invention as defined by the claims.

The present invention provides an optical probe for tissue identification. The probe includes an elongated body. Optical fibers are located within the elongated body for transmitting light to and from the tissue. Light fluctuation protection is associated with the optical fibers. In one embodiment the light fluctuation protection associated with the optical fibers includes a reflective coating on the optical fibers to reduce stray light. In another embodiment the light fluctuation protection associated with the optical fibers includes a filler with very high absorption located within the elongated body between the optical fibers.

The invention is susceptible to modifications and alternative forms. Specific embodiments are shown by way of example. It is to be understood that the invention is not limited to the particular forms disclosed. The invention covers all modifications, equivalents, and alternatives falling within the spirit and scope of the invention as defined by the claims.

BRIEF DESCRIPTION OF THE DRAWINGS

The accompanying drawings, which are incorporated into and constitute a part of the specification, illustrate specific embodiments of the invention and, together with the general description of the invention given above, and the detailed description of the specific embodiments, serve to explain the principles of the invention.

DETAILED DESCRIPTION OF THE INVENTION

Figure 1:
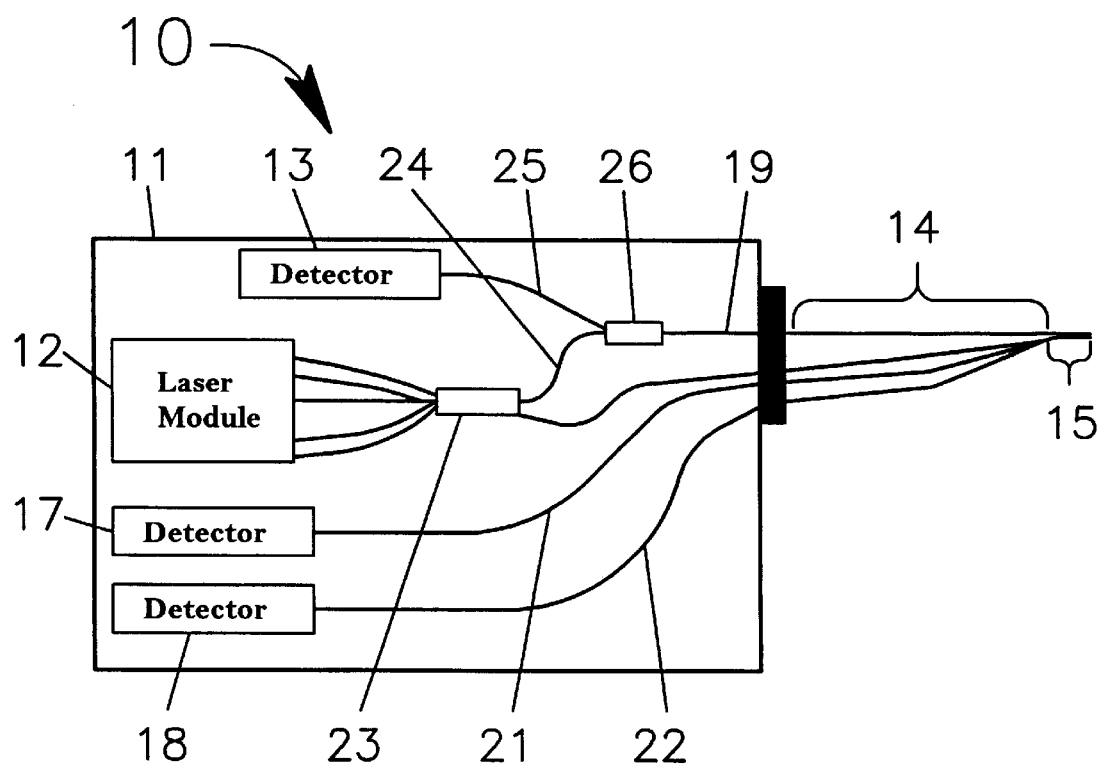
FIG. 1 illustrates an embodiment of a system constructed in accordance with the present invention.

Referring now to the drawings, to the following detailed information, and to incorporated materials; a detailed description of the invention, including specific embodiments, is presented. The detailed description serves to explain the principles of the invention. The invention is susceptible modifications and alternative forms. The invention is not limited to the particular forms disclosed. The invention covers all modifications, equivalents, and alternatives falling within the spirit and scope of the invention as defined by the claims.

Referring now to FIG. 1 an optical probe system, generally designated by the reference numeral 10, is illustrated. A laser module 12 contains multiple laser sources that are each coupled to a fiber optic and probe system. The lasers are combined through a splitter 23 and then split into two outputs 20 and 24.

The output 24, (~90%), from splitter 23 is sent through fiber 24 to splitter 26 and subsequently through fiber 19. Fiber 19 transmits light into an optical probe 15. The fiber optic and probe system obtains information such as biopsy information from tissue. An optical collection fiber 22 within probe 15 delivers light to an optical detector 18. Light that is collected by the emission fiber 19 returns through the splitter 26 and 90% goes into fiber 25 and into detector 13. Detector 13 is used to measure the backscatter or fluorescence. Fluctuations in light delivery to the tip of the device due to cable motion are partly accounted for. These fluctuations occur because losses through the fiber are affected by any changes in the bends in the fiber. This assumes that all the fibers experience similar changes. To increase the probability of this, the fibers within probe 15 should have a similar numerical aperture and material properties. In one embodiment of the invention the fibers are tightly packed and bonded within the cable, see FIG. 3. The fibers within probe 15 can be bonded using a soft polymer compound or silicone. In another embodiment the fibers within probe 15 are covered by a high reflectivity coating, see FIG. 3.

The output 20 from splitter 23 is sent through a reference fiber 20 that takes a small fraction (e.g., 5–10%) of the output. The reference fiber 20 extends to the handle of a probe 15. The other end (21) of the reference fiber 20 is coupled to detector 17. The reference fiber forms a loop (see 20 and 21) that goes from the control unit 11 through the smart probe cable 14, to the smart probe handle and then returns. The reference fiber 20 does not enter the needle section of the smart probe 15. This technique will allow fluctuations in light delivery to the tip of the device due to cable motion to be partly accounted for. These fluctuations occur because losses through the fiber are affected by any changes in the bends in the fiber. This assumes that all the fibers experience similar changes. To increase the probability of this the fibers within probe 15 should have a similar numerical aperture and material properties. In one embodiment of the invention the fibers are tightly packed and bonded within the cable, see FIG. 3. The fibers within probe 15 can be bonded using a soft polymer compound or silicone. In another embodiment the fibers within probe 15 are covered by a high reflectivity coating, see FIG. 3

The intensity at the end of the collection fiber, $I_C$, is related to the laser intensity, $I_0$, the loss through a single pass of the fiber, L, and the effective coupling efficiency between emission and collection fiber, X, through the following expression.

$$I_C \propto I_0 L^2 X;$$

The coupling efficiency, X, includes the geometrical coupling efficiency between the fibers and the tissue absorption and scattering properties. Note that both L and X are wavelength dependent.

The intensity at the end of the reference fiber, $I_R$, is related to the laser intensity, $I_0$, the loss through a single pass of the fiber, L, and the coupling fraction between emission fiber and the reference fiber, A, through the following expression.

$$I_R \propto A I_0 L^2;$$

If we take the ratio of the two intensities we have $$\frac{I_D}{I_R} \propto \frac{X}{A}$$

Using a calibrated laboratory system where we accurately know A, we can determine X in the calibration medium for each probe. This information can be encoded into the device (bar code, etc.) and used by the analysis software to determine A for each probe and system when the probe calibration step is performed by the clinical unit. After this step the device can be used to accurately measure, X, which is related to the tissue properties.

Figure 2:
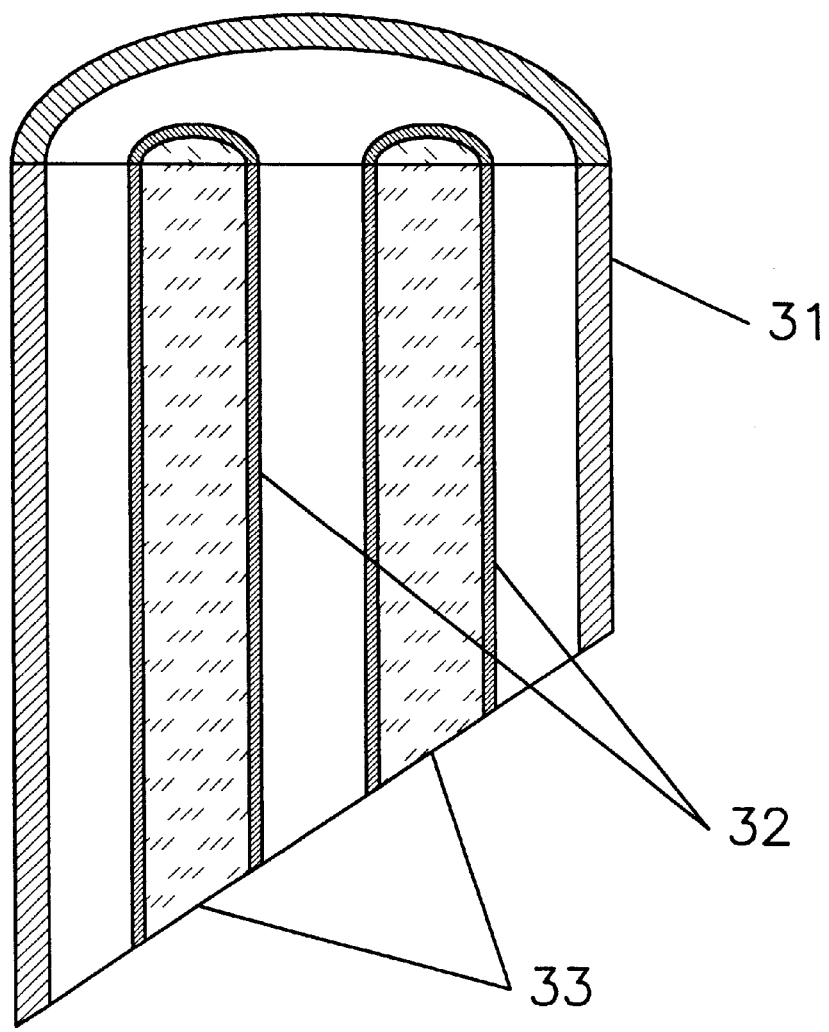
FIG. 2 shows a cross section of the probe of one embodiment of the invention.

Referring now to FIG. 2, an embodiment of the present invention is illustrated by a cross section through an optical probe. The optical probe is generally designated by the reference numeral 30. Optical probe 30 includes an outer layer 31. Optical fibers 33 are contained within the probe 30. In this embodiment the optical fibers 33 are coated with a reflective layer 32. The reflective layer 32 can be any suitable reflective material such as aluminum, chromium, silver, etc. Light that would ordinarily scatter into the optical fibers is prevented from coupling back into the optical fibers by the high reflecting layer 32. A very thin aluminum layer (<1000 angstroms) is considered adequate for most applications; however, other materials such as chromium, silver, etc. may be used.

Figure 3:
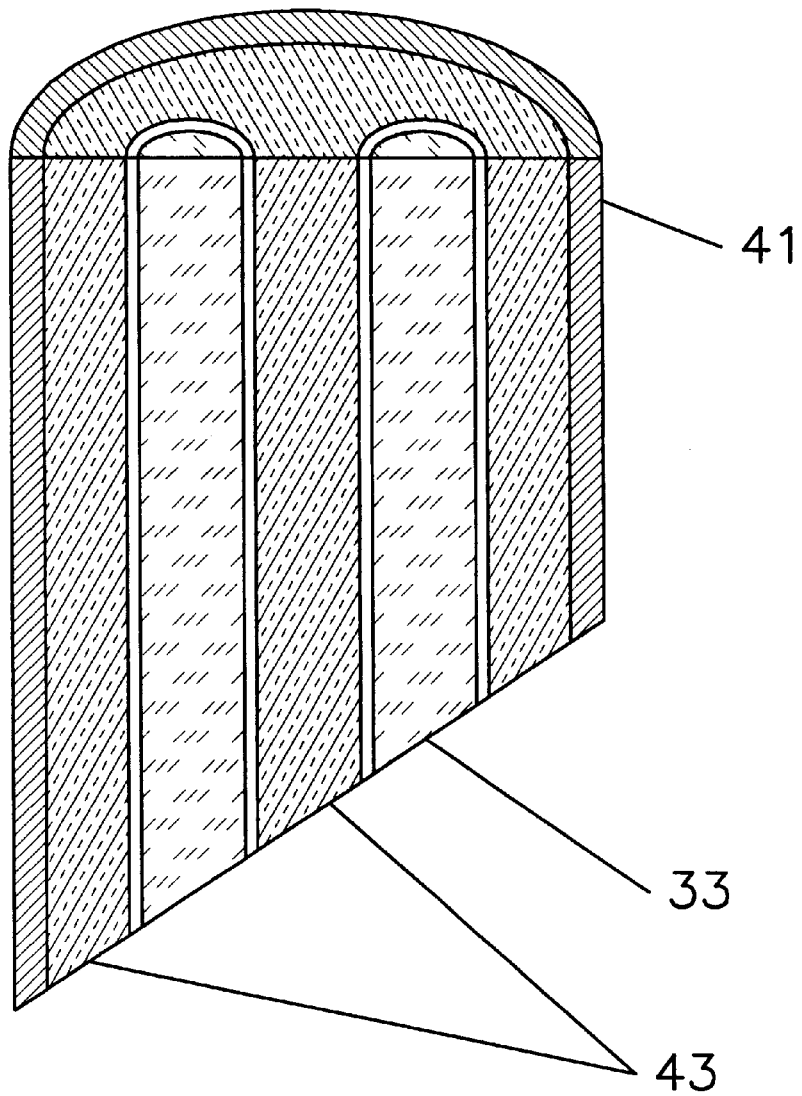
FIG. 3 shows a cross section of the probe of another embodiment of the invention.

Another embodiment of the present invention is illustrated in FIG. 3. The optical probe is generally designated by the reference numeral 40. Optical probe 40 includes an outer layer 11. Optical fibers 42 are contained within the probe 40. Instead of a high reflectivity coating on the optical fiber, a filler 43 with very high absorption is used. This embodiment is more difficult to make effective for all optical wavelengths because high absorption fillers are not available in the mid infrared region.

Figure 4:
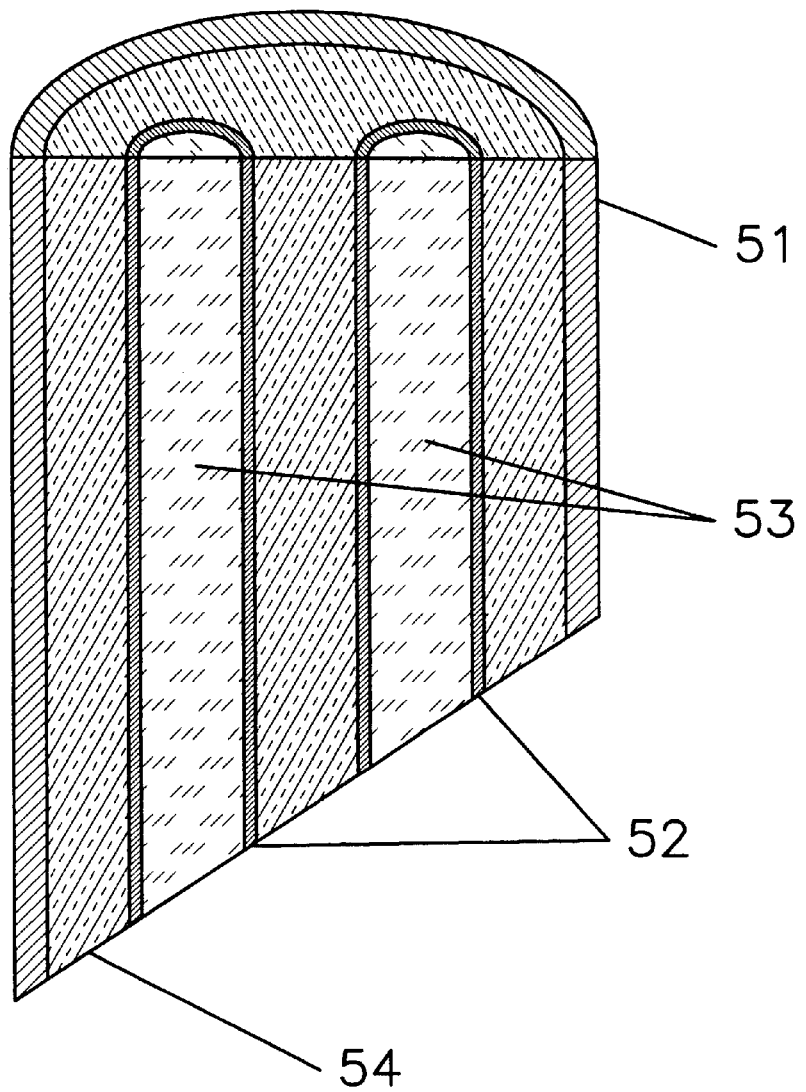
FIG. 4 shows a cross section of the probe of another embodiment of the invention.

Referring now to FIG. 4, another embodiment of the present invention is illustrated by a cross section through an optical probe. The optical probe is generally designated by the reference numeral 50. Optical probe 50 includes an outer layer 51. Optical fibers 53 are contained within the probe 50. The optical fibers 53 are coated with a reflective layer 52. The reflective layer 52 can be any suitable reflective material such as aluminum, chromium, silver, etc. Light that would ordinarily scatter into the optical fibers is prevented from coupling back into the optical fibers by the high reflecting layer 52. A very thin aluminum layer (<1000 angstroms) is considered adequate for most applications; however, other materials such as chromium, silver, etc. may be used. In addition to the high reflectivity coating 52 on the optical fibers 53, a filler 54 with very high absorption is used within the probe 50.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

What is claimed is:

1. An optical probe for tissue identification, comprising:

an elongated body, said elongated body having an internal passage;

a first optical fiber within said elongated body for transmitting light, said first optical fiber located in said internal passage;

a second optical fiber within said elongated body for transmitting light, said second optical fiber located in said internal passage; and a first reflective layer that coats said first optical fiber, a second reflective layer that coats said second optical fiber, and a filler with high absorption within said internal passage for providing light fluctuation protection for said optical probe.

2. The optical probe of claim 1 wherein said first reflective layer and said second reflective layer is aluminum, chromium or silver.

3. The optical probe of claim 1 wherein said first reflective layer and said second reflective layer is aluminum.

4. A multisensor probe for tissue identification comprising:

an elongate body having an internal passage and a distal a distal tip, an optical scattering and absorption spectroscopy sensor configured to deliver and receive light from said distal tip, a first optical fiber extending through said internal passage of said elongate body to said distal tip, a second optical fiber extending through said internal passage of said elongate body to said distal tip, and a first reflective layer that coats said first optical fiber, a second reflective layer that coats said second optical fiber, and a filler with high absorption within said internal passage for providing light fluctuation protection for said multisensor probe.

5. The multisensor probe of claim 4 wherein said first reflective layer and said second reflective layer is aluminum, chromium or silver.

6. The multisensor probe of claim 4 wherein said first reflective layer and said second reflective layer is aluminum.

7. The multisensor probe of claim 4 wherein said first reflective layer and said second reflective layer is a very thin layer of aluminum.

8. The multisensor probe of claim 4 wherein said first reflective layer and said second reflective layer is chromium.

9. The multisensor probe of claim 4 wherein said first reflective layer and said second reflective layer is silver.

* * * * *